United States Patent
Gertler et al.

[11] Patent Number: 5,954,745
[45] Date of Patent: Sep. 21, 1999

[54] CATHETER-FILTER SET HAVING A COMPLIANT SEAL

[76] Inventors: Jonathan Gertler, 16 Greenridge Rd.; Roger Kamm, 31 Nonesuch Rd., both of Weston, Mass. 02193

[21] Appl. No.: 09/079,816

[22] Filed: May 15, 1998

Related U.S. Application Data

[60] Provisional application No. 60/046,777, May 16, 1997, and provisional application No. 60/057,439, Sep. 2, 1997.

[51] Int. Cl.⁶ .................................................. A61M 29/00
[52] U.S. Cl. ........................ 606/200; 604/96; 604/101; 606/194; 606/159
[58] Field of Search ............................... 606/1, 191, 194, 606/159, 198, 200; 604/96, 101; 128/898, 899

[56] References Cited

U.S. PATENT DOCUMENTS

| | | |
|---|---|---|
| 3,952,747 | 4/1976 | Kimmell, Jr. . |
| 4,723,549 | 2/1988 | Wholey et al. . |
| 4,794,928 | 1/1989 | Kletschka . |
| 4,873,978 | 10/1989 | Ginsburg . |
| 5,053,008 | 10/1991 | Bajaj ........................................ 606/200 |
| 5,329,942 | 7/1994 | Gunther et al. . |
| 5,443,449 | 8/1995 | Buelna . |
| 5,470,314 | 11/1995 | Walinsky . |
| 5,662,671 | 9/1997 | Barbut et al. . |
| 5,695,518 | 12/1997 | Laerum . |
| 5,695,519 | 12/1997 | Summers et al. . |
| 5,725,550 | 3/1998 | Nadal . |
| 5,769,816 | 6/1998 | Barbut et al. ........................... 606/200 |
| 5,814,064 | 9/1998 | Daniel et al. ........................... 606/200 |

FOREIGN PATENT DOCUMENTS

WO 95/05209  2/1995  WIPO .

Primary Examiner—Michael Buiz
Assistant Examiner—William Lewis
Attorney, Agent, or Firm—Bromberg & Sunstein LLP

[57] ABSTRACT

A catheter-filter set in an embodiment may be used in a vas through which a biological fluid may flow. This embodiment includes a tubular member, having a lumen disposed along its length and an insertion end for insertion into the vas. The lumen defines a longitudinal axis and a radial direction perpendicular thereto. The embodiment also has a filter, coupled to the tubular member and having a circumference, for trapping undesired particles. Finally, the embodiment includes a resilient member, having compliance in the radial direction, disposed circumferentially about the filter and, when deployed in the vas, forms a seal against the interior wall of the vas. Other embodiments are also provided.

31 Claims, 9 Drawing Sheets

CATHETER-FILTER SET HAVING A COMPLIANT SEAL

RELATED U.S. APPLICATION(S)

The present application claims priority from Provisional Application Serial No. 60/046,777, filed May 16, 1997, and from Provisional Application Serial No. 60/057,439, filed Sep. 2, 1997, both of which are hereby incorporated herein by reference.

TECHNICAL FIELD

The present invention relates to catheter-filter sets, including those for use in angioplasty and other procedures.

BACKGROUND ART

A large number of medical procedures utilize catheters. A catheter is defined herein and within the appended claims as a tubular, flexible instrument for insertion into a body cavity. Catheters may facilitate the withdrawal or introduction of fluids or other substances and may, in combination with other coupled components, perform a variety of other useful functions.

Catheters coupled with inflatable balloons provide the means to facilitate the unblocking of and the relief of constriction within various body passageways and vessels. Such angioplasty procedures can replace other more invasive surgical procedures and provide acceptable solutions to correct life threatening conditions. However, these procedures carry a risk of serious secondary problems associated with the transmission of unwanted material downstream of the operative site. Any material, such as plaque built up in arterial vessels, which does not adhere to the interior vas wall or is in another way removed from the vessel following treatment becomes a likely source of downstream blockage. In arterial angioplasty, embolic ischemic damage distal to the angioplasty site is a major complication of the procedure. Mobile arterial plaque is, a major factor linked with ischemic stroke or end organ/limb infarction. In particular, carotid artery angioplasty is not a favored practice at present due to the risk of emboli and resulting stroke.

Some catheters coupled with downstream filtering capability have been previously disclosed. Several utilize wire mesh filters which are generally not compliant and do not accommodate localized changes in vessel diameter and shape which may be caused by on-going fluid flow restoration and pulsatility. Other designs contain deployment structures which may make insertion prior to and retraction after completion of a procedure problematic or unduly risky.

Typical prior art catheter arrangements are disclosed in U.S. Pat. Nos. 4,723,549; 4,794,928; 5,662,671; and 5,695,519. These documents are hereby incorporated herein by reference.

SUMMARY OF THE INVENTION

Various embodiments of the present invention solve problems of the prior art by providing radial compliance to accommodate localized changes in vessel diameter and shape which may be caused by on-going fluid flow restoration and pulsatility. Furthermore, some embodiments of the invention provide a device that is biased to return to its lowest profile condition in the absence of active operator input to facilitate making arterial angioplasty, particularly in the cerebral and coronary beds, more fail-safe. Various embodiments of the invention avoid asperities or protrusions which can traumatize or otherwise damage or irritate interior vas walls. Similarly various embodiments provide for cushioning of the filter element against the vas wall when it is deployed. This cushioning effect is balanced with the requirement of effective sealing of the vas to prevent any unwanted downstream flow of matter.

Accordingly, in a first embodiment of the invention there is provided a catheter-filter set for use in a vas through which a biological fluid may flow. This embodiment includes a tubular member, having a lumen disposed along its length and an insertion end for insertion into the vas. The lumen defines a longitudinal axis and a radial direction perpendicular thereto. The embodiment also has a filter, coupled to the tubular member and having a circumference, for trapping undesired particles. (Unless the context otherwise requires, the term "particles" as used in this description and the accompanying claims refers to substances to be removed from a vas, and may include thrombotic material.) Finally, the embodiment includes a resilient member, having compliance in the radial direction, disposed circumferentially about the filter and, when deployed in the vas, forming a seal against the interior wall of the vas. In further embodiments, the resilient member may be inflatable, such as a balloon, or alternatively may be an O-ring or sleeve. The outer surface of the resilient member may form the seal with the interior wall or may otherwise effectuate the seal. In a related embodiment the resilient member is a balloon having an anterior for receiving an inflation fluid and a shape so that when the balloon is inflated there is provided a passageway permitting fluid flow through the filter. In accordance with another related embodiment, the balloon is toroidal in shape and may have anisotropic elasticity so that during inflation its interior cross-section expands relatively less than its radial extent. Alternatively or in addition, the catheter-filter set may include an elastic member coupled to the balloon and the tubular member for causing the balloon to be radially confined when not deployed. In yet another variation, regardless whether a balloon is utilized, the filter has a stowed position where the filter is radially confined and disposed in the lumen so that the catheter-filter set may be inserted into and removed from the vas, and a deployed position, where the filter is radially expanded.

Various embodiments of the present invention have a range of potential applications. The application of embodiments to angioplasty procedures will be apparent to those skilled in the art. In addition, through either standard open technique or laparoscopic technique, retrieval of common duct s,tones in the biliary tree is facilitated by catheter passage utilizing embodiments herein. Similarly, through either standard open technique or cystographic technique, retrieval of ureteral and bladder duct stones is, also, facilitated by catheter passage via endoscopic or surgical methods. A catheter coupled with an inflatable balloon may also be utilized to effect balloon sphincteroplasty and stone retrieval. Embodiments herein provide improved devices to effectively retrieve such stones and to avoid their further passage or migration downstream. Embodiments herein may also employable as a temporary filtering device for the vena cava. In the process of lytic treatment for deep venous thrombosis, there is a risk of clot (thrombus) breaking loose and causing pulmonary embolism, a potentially fatal event. Although filters exist for vena cava use, these are permanent structures with attendant long term morbidity. Having an effective and retractable filter which is in place only for the time of significant risk, i.e., during deep venous clot lysis, would allow protection from pulmonary embolism and avoidance of the long term sequelae of a permanent filter insertion.

Discussion of medical procedures and associated devices in this description may focus, for example, upon arterial (blood circulation), biliary, and ureteral systems. This focus in no way limits the applicability of embodiments herein to any and all other uses for catheters with filtration capability known to those skilled in the art.

In another embodiment, there is provided a catheter-filter set having a tubular member, which has a first lumen disposed along its length, an insertion end for insertion into and a retraction end for retraction out of the vas. The lumen defines a longitudinal axis and a radial direction perpendicular thereto. The embodiment also has a filter, coupled to the tubular member proximal to the insertion end, wherein the filter has a stowed position and a deployed position, and a non-inflatable actuator, coupled to the filter, for causing the filter to move from the stowed position to the deployed position, wherein, absent operation of the actuator, the filter is biased to be in the stowed position. In a related embodiment, the set also includes a vas conditions-modifying element located upstream from the filter; this element may be an angioplasty balloon. In yet another related embodiment, the tubular member has a second lumen having an inlet upstream from the vas conditions-modifying element and an outlet downstream from the filter, permitting unimpeded, downstream fluid flow to bypass the filter. In further embodiment, the set has a plurality of resilient ribs, each rib having a first end coupled to the tubular member, each rib also coupled to the filter, the ribs having a stowed condition in which they are parallel to the longitudinal axis and a deployed condition in which at least a portion of each rib is disposed radially outward from the tubular member. Each rib may have a second end slidably mounted on the tubular member and coupled to the actuator. The catheter-filter set may further include a resilient member, having compliance in the radial direction, disposed circumferentially about the filter and, when deployed in the vas, forming a seal against the interior wall of the vas.

In another embodiment in accordance with the present invention, there is provided a catheter-filter set having:

a. a tubular member, having a lumen disposed along its length, an insertion end for insertion into and a retraction end for retraction out of the vas, the lumen defining a longitudinal axis and a radial direction perpendicular thereto; and b. a filter, coupled to the tubular member proximal to the insertion end, wherein the filter has a stowed position wherein the filter is radially confined and disposed in the lumen so that the catheter-filter set may be inserted into and removed from the vas, and a deployed position, wherein the filter is radially expanded.

DETAILED DESCRIPTION OF SPECIFIC EMBODIMENTS

Various embodiments of the catheter-filter set described herein address a number of shortcomings inherent in previous designs. Some desirable features for the filter portion of the set are that it be easily confined in a radial direction for ease of set insertion and removal, that it be capable of capturing and safely removing all particles flowing downstream in a vas, and additionally, it should be designed so as to minimize the risk of accidental deployment and to collapse into position for removal in the event of failure. It should be atraumatic to the native vas wall and should accommodate changes in vas diameter.

Figure 1B:
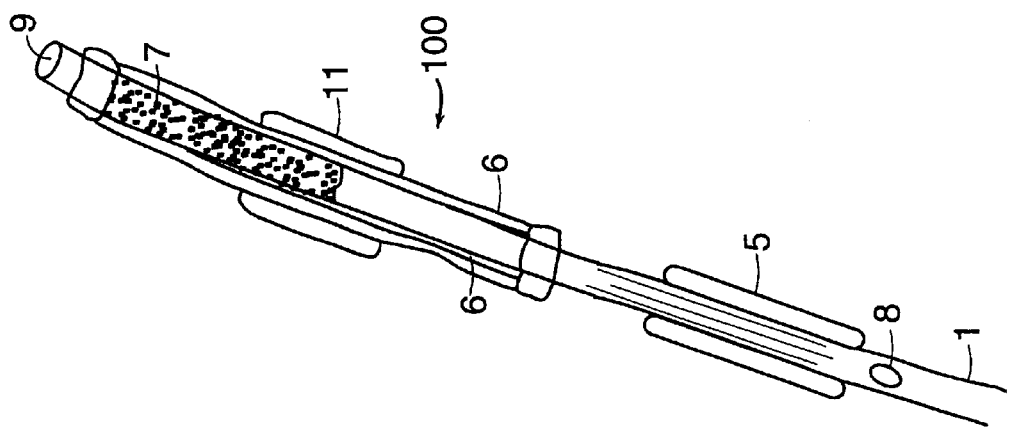
FIGS. 1A and 1B are longitudinal views of a catheter-filter set, in the deployed and the stowed conditions, respectively, used in a vas as part of an angioplasty device and using a toroidal balloon according to an embodiment of the invention.
Figure 1A:
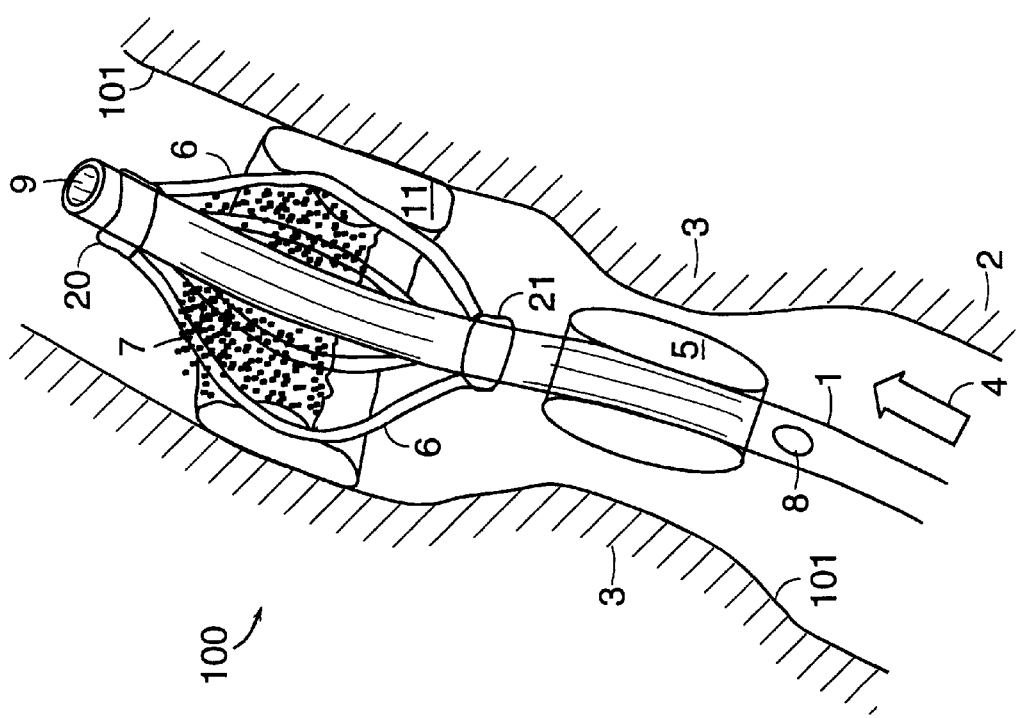

FIGS. 1A and 1B are longitudinal views of a catheter-filter set, in the deployed and the stowed conditions, respectively, used in a vas as part of an angioplasty device and using a toroidal balloon according to an embodiment of the invention. FIG. 1A shows a catheter 1 inserted into a vas 2. The vas may be constricted or otherwise blocked at a location 3. Downstream fluid flow is indicated by arrow 4. An angioplasty balloon 5 affixed to the catheter and inflatable (by means well known in the art) is positioned proximate to location 3. During and after the angioplasty balloon 5 inflation process, unwanted particles may flow downstream from location 3. A plurality of resilient ribs 6 (four are shown in this view) are coupled to the catheter 1 by two collars, one collar 20 at a downstream end and the other collar 21 at an opposing, upstream end of the catheter. In this embodiment, one of collars 20 and 21 is fixed relative to the catheter 1 and the other of the collars is free to slide along the catheter 1. The ribs 6 and both collars 20 and 21 are positioned at a location downstream from location 3 and the angioplasty balloon 5. A filter 7 is shown attached to the ribs 6 and to the catheter 1. A toroidal balloon 11, which is distinct from the angioplasty balloon 5, is attached to the ribs 6. In this embodiment, the toroidal balloon 11 is mounted approximately midway along the length of the ribs 6 and positioned radially outward from the catheter 1. (The filter 7 is represented in this figure and figures below by a dot or hash pattern; for clarity of representation, the dot or hash pattern is not shown to occupy the entire region occupied by the filter. It will be understood, however, that when deployed the filter, tog;ether with any accompanying structure, such as the balloon 11, will occupy the entire cross section of the vas so as to operate in an effective manner known in the art.)

FIG. 1B shows that, in accordance with the embodiment in the stowed condition, the ribs parallel to the longitudinal axis of the catheter 1 facilitating set 100 insertion into and retraction out of the vas 2 minimizing trauma to the vas wall 101. During insertion and retraction of set 100 and catheter 1 into and out of the vas 2, the uninflated toroidal balloon 11 is collapsed and radially confined against the ribs 6 and the uninflated angioplasty balloon 5 is collapsed against the catheter 1. As illustrated in FIG. 1A, when the toroidal balloon 11 is inflated (in accordance with means well known in the art), one of collars 20 and 21 slides toward the other collar causing at least a portion of each of the ribs 6 and the filter 7 to be disposed radially outward from the catheter 1. The toroidal balloon 11 effectively spans any radial distance between, on the one hand, the vas wall 101, and on the other hand, the ribs 6 with the expanded filter 7. The toroidal balloon 11 thus forms a compliant seal between the set 100 and the vas wall 101.

After this compliant seal has been established, the angioplasty balloon 5 may then be inflated to unblock the vas 2 at location 3. The deployed filter 7 may then capture unwanted particles flowing downstream during and after operation and subsequent deflation of the angioplasty balloon 5. After the procedure, the toroidal balloon 11 is deflated, and the set 100 returns to the position shown in FIG. 1B for retraction from the vas 2. Unwanted particles are trapped within the filter 7 and are safely removed from the vas 2 upon retraction of the set 100. Additionally, biasing components (for example, as discussed below in connection with later figures) may be used in connection with the set 100 to insure the return to the position shown in FIG. 1B after deflation of the toroidal balloon 11. These components may include, and are not limited to, elastic bands coupled to one or more elements of the ribs 6, the filter 7, and collars 20 and 21.

Also shown in FIG. 1A, an inlet port 8 is provided by the catheter 1 at a location upstream from the angioplasty balloon 5 and an outlet port 9 is provided downstream from the filter 7. The ports are in communication with a lumen of the catheter; the lumen may be the same as the lumen used for other purposes or may be a separate dedicated lumen. The result of this structure is an autoperfusion pathway from inlet port 8 through a catheter lumen to the outlet port 9 to permit the unimpeded flow of a quantity of fluid during the time in which the medical procedure is being performed. The feature is advantageous when deleterious results may occur from even short intervals of downstream fluid starvation or depletion. Hypoperfusion during angioplasty balloon inflation is primarily relevant to the cerebral and coronary beds. Carotid artery angioplasty, in which the brain is immediately downstream from the location 3, is a prime example of a procedure benefiting from an auto-perfusion pathway. In many arterial applications, given the normal magnitude of blood pressures, there may be provided a lumen having an internal diameter of 1 to 2 mm. Even when blood flow is not as high as normal, the reduced rate of flow may nevertheless significantly reduce the risk of tissue damage caused by a complete interruption of flow in the cerebral and coronary beds.

Figure 2A:
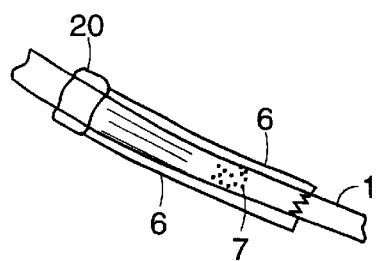
FIGS. 2A and 2B are longitudinal views of a portion of a catheter-filter set, in the stowed and the deployed conditions, respectively, illustrating generally filter deployment according to an embodiment of the invention utilizing ribs for structuring the filter.
Figure 2B:
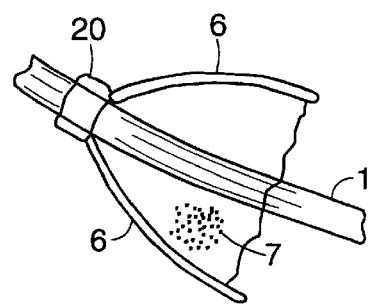

FIGS. 2A and 2B are longitudinal views of a portion of a catheter-filter set, in the stowed and the deployed conditions, respectively, illustrating generally filter deployment according to an embodiment of the invention utilizing ribs 6 for structuring the filter 7. FIG. 2A shows the ribs 6 and the filter 7 coupled to and juxtaposed with the catheter 1 in conjunction with the downstream collar 20. In FIG. 2B the ribs 6, which are resilient, are expanded radially from the catheter 1 to form a convex shape. The expanded ribs 6 support the filter 7 as shown. Preferably, the ribs 6 are free from asperities. The ribs 6 may be made of any resilient material with sufficient rigidity to support and to enable deployment of the filter 7. The number of ribs 6 may be selected to be sufficiently large to facilitate a seal of the filter 7 with the interior wall of the vas 2 but not so numerous as to significantly obstruct fluid flow or convenient operation of the set. In the embodiment of FIGS. 2A and 2B, the ribs 6 are disposed radially outward from the filter 7. In other embodiments of the invention, the ribs 6 may be disposed radially inward from the filter 7, so that, when stowed, the resilient ribs 6 lie immediately adjacent to the catheter 1. Such other embodiments may deploy in a fashion analogous to opening of an umbrella. The ribs 6 may have one free end as in FIGS. 2A and 2B, or be coupled to the catheter 1 at both ends and bow in the middle for deployment as for example in FIGS. 1A and 1B. The filter 7 may beneficially be made of a porous, compliant material in a manner known in the art. Suitable materials may include, but are not limited to, woven nylon, plastic resins such as PTFE sold under the Teflon trademark by Dupont of Wilmington, Delaware, other woven polymer, porous silicone rubber and latex rubber. Suitable materials are sufficiently porous to permit a small downstream flow of fluid yet capable of collecting any dangerous particles. For example, calculations suggest that, for an arterial application, a woven material with a fiber porosity of 90% and a spacing of 200 microns may pose little impediment to normal blood flow while trapping undesirable particles.

Figure 3A:
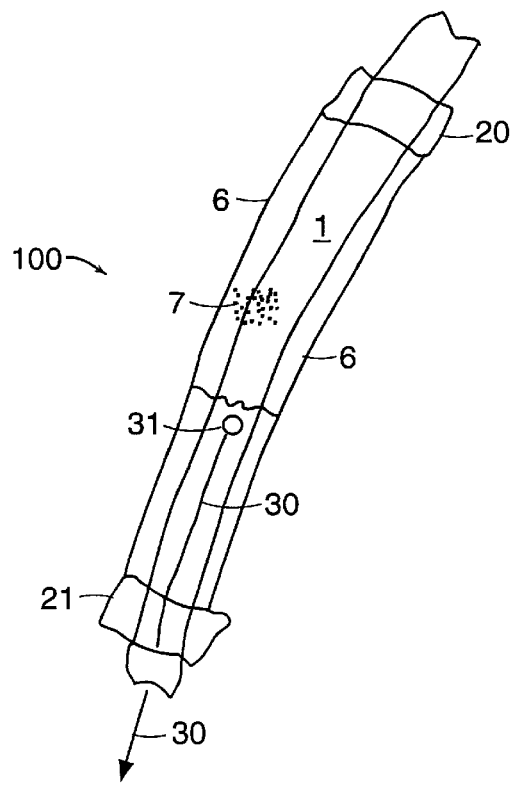
FIGS. 3A and 3B are longitudinal views of a catheter-filter set, in accordance with a tether deployment embodiment of the invention, showing stowed and deployed conditions, respectively.
Figure 3B:
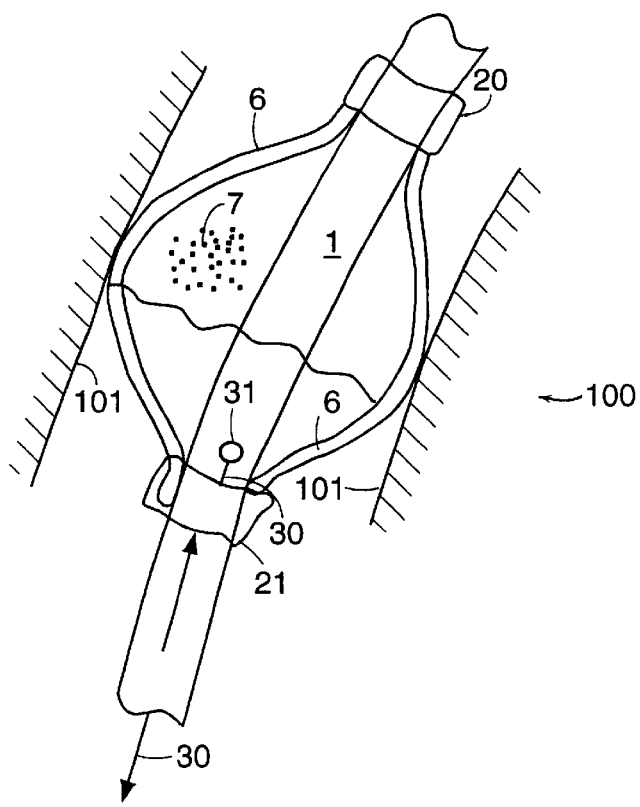

FIGS. 3A and 3B are longitudinal views of a catheter-filter set, in accordance with a tether deployment embodiment of the invention, showing stowed and deployed conditions, respectively. As shown in FIG. 3B, the ribs 6 of this embodiment are attached to the catheter 1 at both ends by collars 20 and 21. The upstream end collar 21 is free to slide along the catheter 1 while the downstream end collar 20 is fixed. Collar 21 is tethered with line 30 so that an operator can, by applying an upstream force to line 30 slide collar 21 downstream toward collar 20. This action urges the ribs 6 to form a convex shape and to expand radially from the catheter 1. As FIGS. 3A and 3B show, tethering may be accomplished by attaching one end of line 30 to collar 21, feeding the line 30 through a port 31 provided by the catheter 1 at a position downstream from collar 21. The line passes into a lumen of the catheter and exits ithe catheter 1 upstream at its retraction end. The ribs 6 may expand to the full radial extent of the vas 2. Other material, as discussed in connection with other figures, may be coupled to the ribs 6 proximate to their approximate midpoint in length to provide better sealing action and cushioning at the interface with the vas wall 101. (For example, the toroidal balloon of FIGS. 1A and 1B may be employed; alternatively, any suitable resilient sleeve or O-ring may be utilized.) The ribs 6 will return to the stowed position of FIG. 3A, in accordance with the embodiment of the invention, with the elimination of the applied upstream force on line 30. This provides a set 100 which is biased to remain in and revert to the stowed position. Such bias provides for assured collapsibility upon retraction and offers a high degree of fail-safe operation by minimizing the chance of accidental deployment.

Figure 4A:
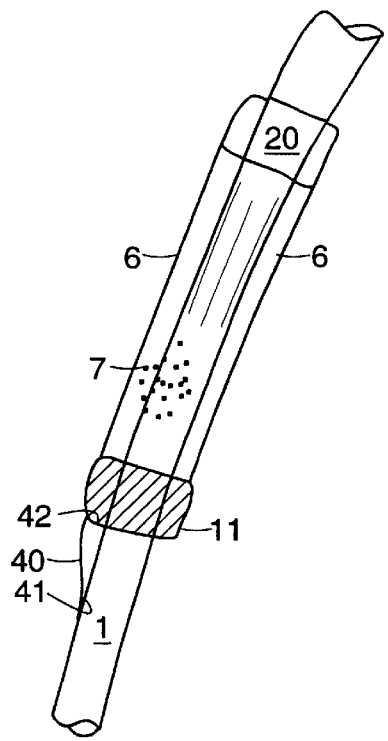
FIGS. 4A and 4B are longitudinal views of a catheter-filter set, in accordance with a balloon deployment embodiment of the invention, showing stowed and deployed conditions, respectively.
Figure 4B:
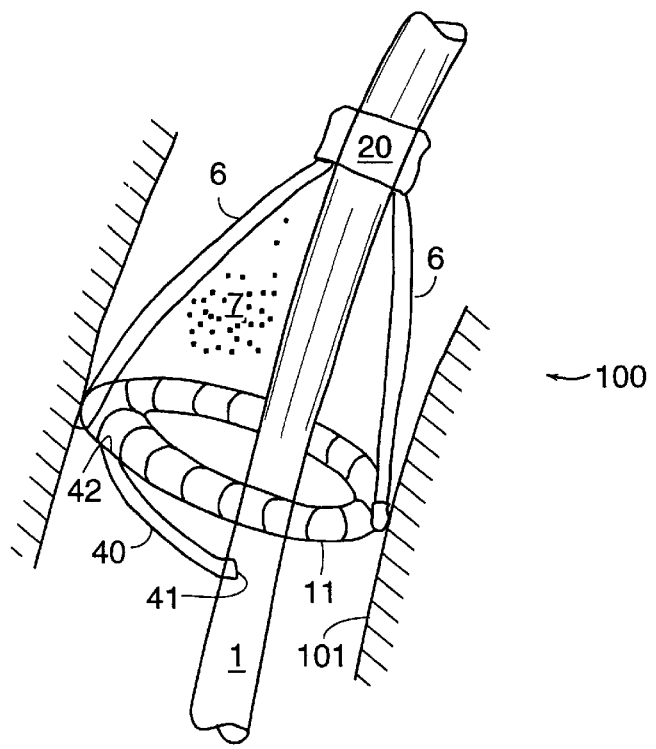

Another embodiment according to the invention provides, a filter deployment technique using an inflatable toroidal balloon 11 with ribs 6 which have their upstream end uncoupled to the catheter 1. The stowed position is shown in FIG. 4A; the deployed position in FIG. 4B. Operation of this embodiment is similar to that of FIGS. 1A and 1B with respect to the use of a toroidal balloon and to that of FIGS. 2A and 2B with respect to the ribs 6. A tube 490 is provided for inflation fluid communication between a lumen disposed within the catheter 1 and the toroidal balloon 11. The opposing ends of tube 40 are, respectively, inserted and remain within ports 41, provided by the catheter 1, and 42, provided by the toroidal balloon 11. The ends of tube 40 may be secured in the ports 41 and 42 with adhesives or using other methods in a manner known in the art. The uninflated toroidal balloon 11, as shown in FIG. 4A is coupled to the upstream ends of the ribs 6 and juxtaposed with the catheter 1. As shown in FIG. 4B, with inflation of the toroidal balloon 11, the resilient ribs 6 expand radially from the catheter 1 to form a convex shape supporting the filter 7. At its most radially outward extent, the inflated toroidal balloon 11 effects a compliant seal between the set 100 and the vas wall 101. The toroidal balloon 11 may be made by wrapping fiber around it so that its expansion will be constrained in such a way that the diameter of its inflatable cross-section increases to a lesser degree than its radial (perpendicular to the catheter axis) dimension. In fact, this mode of inflation can be produced by any material that is anisotropic having a high stiffness (or Young's modulus) in the direction of the fiber wrapping and a low stiffness in the direction perpendicular to the wrapping. The inflation of the toroidal balloon provides the necessary structural rigidity needed to withstand the forces associated with downstream fluid flow (in particular, arterial blood flow) while the set 100 is in the deployed condition.

Figure 5:
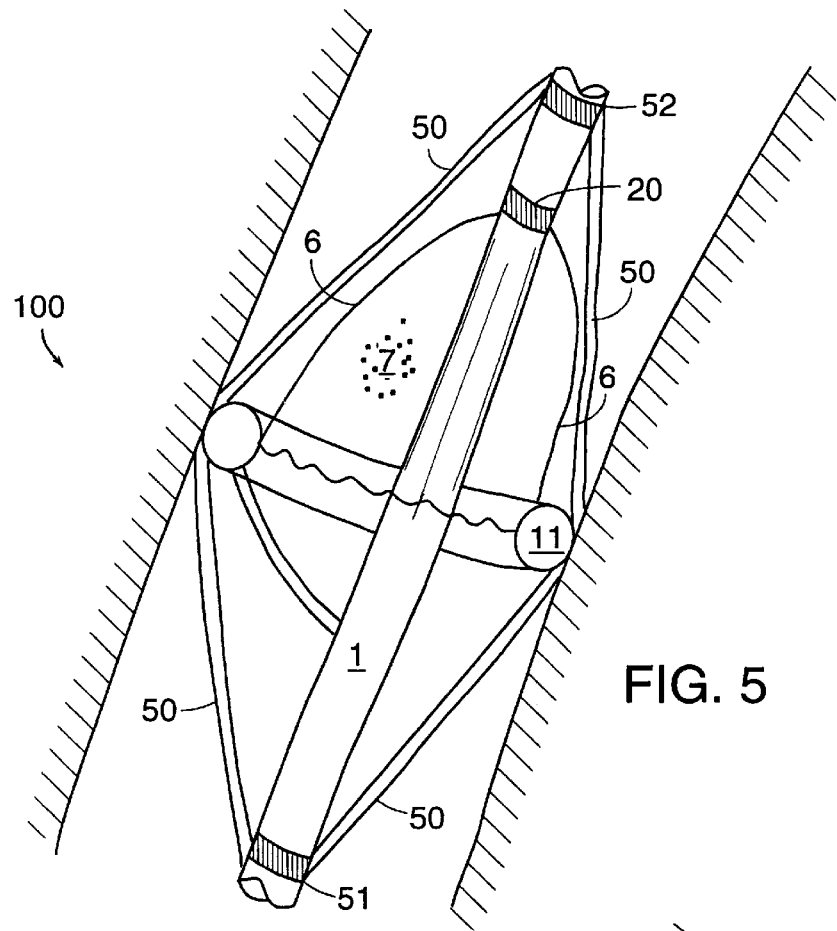
FIG. 5 is a longitudinal view of a catheter-filter set in accordance with an embodiment using balloon deployment wherein elastic bands bias the set in a stowed condition.

FIG. 5 is a longitudinal view of a catheter-filter set in accordance with an embodiment using balloon deployment wherein elastic bands 50 are employed to bias the set in a stowed condition. The bands 50 are coupled to an upstream collar 51 and a second downstream collar 52. Both collars 51 and 52 are coupled to the catheter 1; the second downstream collar 52 is positioned at a distance farther downstream along the catheter 1 than collar 20 to which optional ribs 6 may be coupled. This embodiment provides a set 100 which is biased to revert to the stowed condition. On deflation of the toroidal balloon 11, the bands 50 act to force the balloon 11, the ribs 6, and the filter 7, with any entrapped particles within, to revert to the stowed condition for safe retraction.

Figures 6A, 6B:
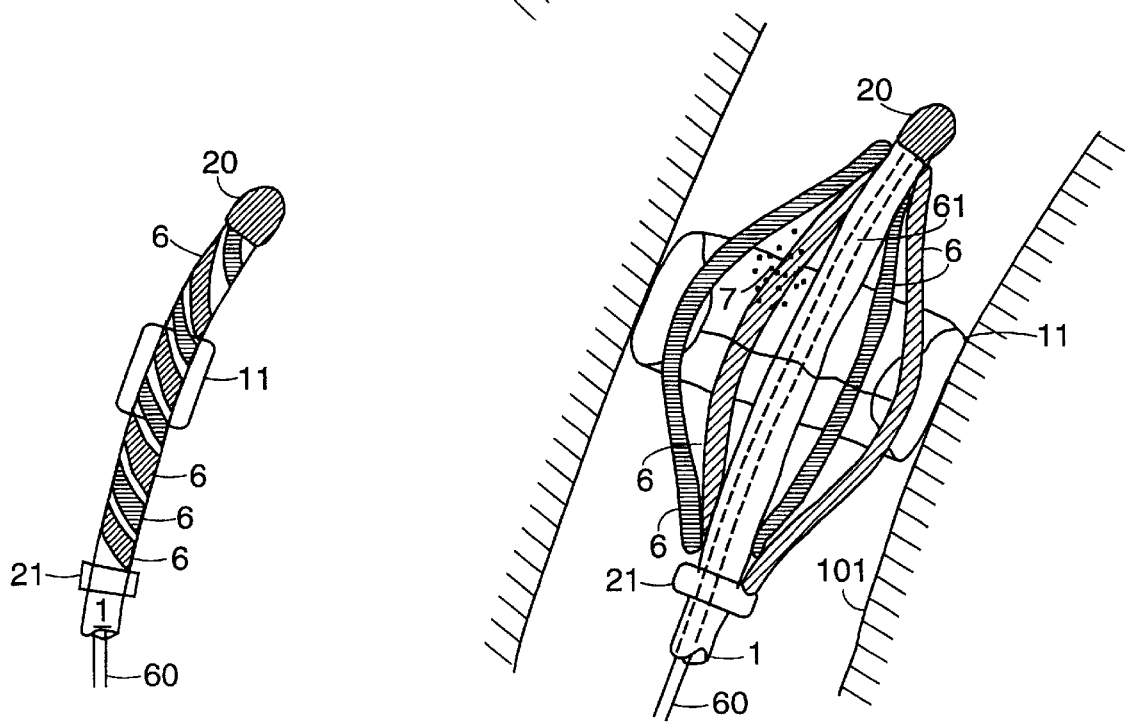
FIGS. 6A and 6B are stowed and deployed conditions respectively of an embodiment similar to that of FIGS. 4A and 4B, but wherein the ribs are normally twisted in a stowed condition, in which the embodiment is biased.

FIGS. 6A and 6B are stowed and deployed conditions respectively of an embodiment similar to that of FIGS. 4A and 4B, but wherein the ribs are normally twisted in a stowed condition, in which the embodiment is biased. The ribs 6 (which are here differently shaded to permit differentiation in the figure), when in a relaxed, unstressed configuration, fit snugly about the catheter 1 bore in a helical arrangement, as shown in FIG. 6A. The filter 7 is gathered together inside the ribs while the cushioning balloon 11 lies outside the ribs 6 but deflated into a collapsed configuration. The ribs 6 in this embodiment are attached at both the upstream and downstream ends to collars 21 and 20 respectively. The collars 21 and 20 are constrained so as to prevent movement in the longitudinal direction, but the downstream collar 20 can be rotated by rotation of a stiff line 60 threaded through a lumen 61 of the catheter 1. Rotation of the downstream collar 20 causes the ribs 6 to bow outward into the deployed position illustrated in FIG. 6B. Once deployed, the balloon 11 can be inflated to provide a resilient seal against the interior wall of the vas 101 while maintaining an open space between the balloon 11 and catheter 1 for fluid flow. Bowing of the ribs deploys the filter 7 attached to the inner surface of the balloon 11 so that it can function as a trap for debris released from an upstream site. Retraction of the ribs 6 occurs when the stiff line 60 is allowed to rotate back to its original position and the balloon 11 is deflated. The filter set is therefore biased closed in that when pressure is relieved from the balloon 11 and the torque exerted on the stiff line 60 is released, the ribs 6 and filter 7 revert to their stowed position.

Figure 7A:
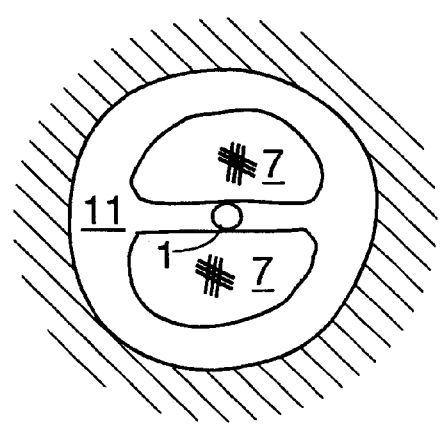
FIG. 7A is a cross-sectional view of a catheter-filter set in the deployed condition illustrating a balloon deployment design according to an embodiment of the invention in which the balloon has a passageway to permit fluid flow therethrough.
Figure 7B:
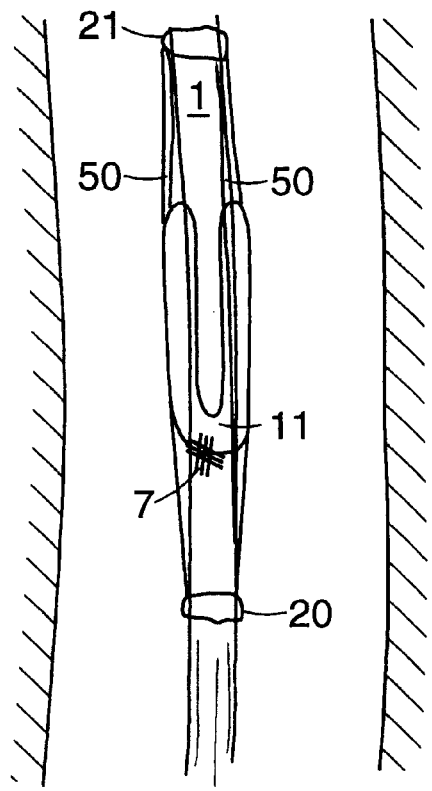
FIGS. 7B and 7C are longitudinal views of the same embodiment in the stowed and the deployed conditions, respectively.
Figure 7C:
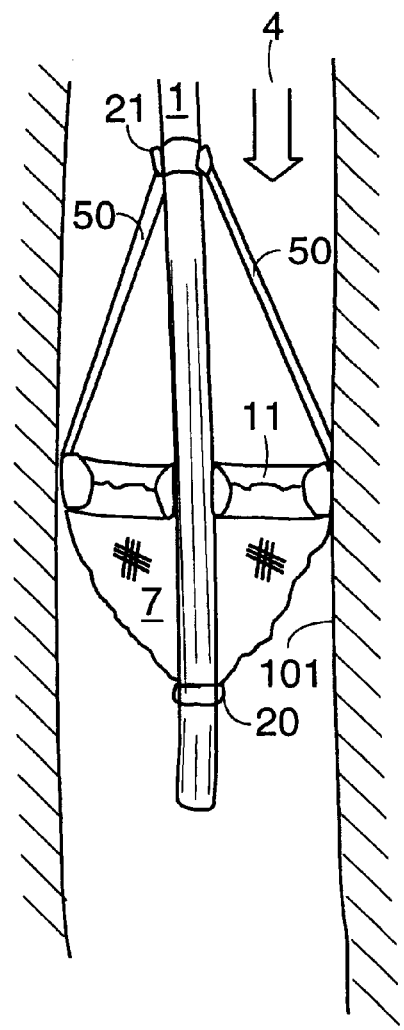

FIG. 7A is a cross-sectional view of a catheter-filter set in the deployed condition illustrating a balloon deployment design according to in embodiment of the invention in which the balloon has a passageway to permit fluid flow therethrough. FIGS. 7B and 7C are longitudinal views of the same embodiment in the stowed and the deployed conditions, respectively. In this embodiment, the inflation balloon 11 takes on the shape of two "Ds" back-to-back. The advantage of this embodiment is that the catheter 1 passes directly through the inflatable portion of the balloon 11, avoiding the need for a separate inflation line that might be prone to rupture because of its small diameter. FIG. 7A shows the balloon in a view along the axis of the vas 2 looking in the downstream direction. The catheter 1 can be seen passing through at the center, and is sealed to the balloon at the points where it passes through the balloon membrane. The catheter has a port inside the balloon 11 that is used for balloon inflation. The filter 7 is seen in FIG. 7A through the openings in the balloon 11 through which the fluid is free to flow. FIG. 7B shows the balloon 11 in the retracted or stowed position. Elastic bands 50 hold the deflated balloon 11, so that it is radially confined, tight against the catheter 1. The filter 7 is gathered together and held against the catheter 1 in part by the elastic bands 50. Deployment is accomplished by inflation of the balloon 11, a process that forces the balloon 11 into its double-D shape shown in longitudinal view in FIG. 7C. The inflated balloon 11 of FIG. 7C forms a flexible seal against the vas wall 101 and deploys the filter 7. The filter in this embodiment is firmly tethered to the catheter at its downstream end to aid in gathering the filter 7 to the catheter on balloon deflation. The balloon 11 is made from a flexible but relatively inextensible polymer so that on inflation, it takes the shape shown.

Figure 8A:
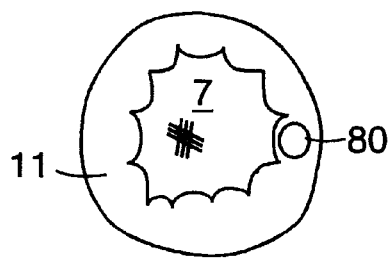
FIG. 8A is a cross-sectional view of a catheter-filter set according to an embodiment of the invention, using for deployment a balloon 11 that is asymmetrically disposed with respect to the tubular member.
Figure 8C:
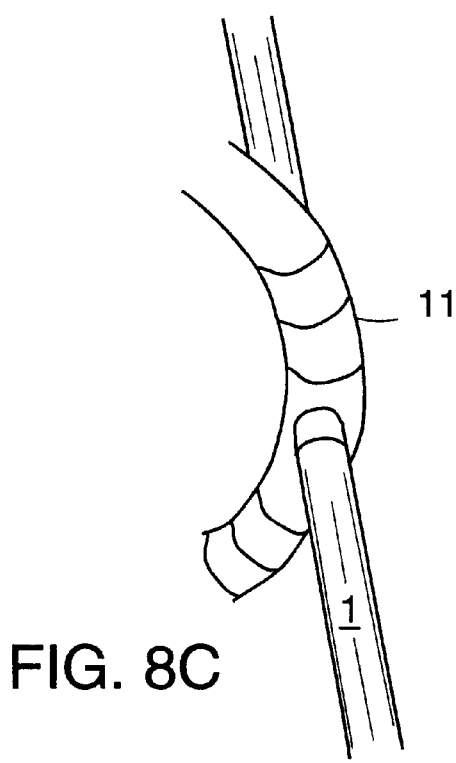
FIG. 8C shows detail of the catheter-balloon interface.
Figure 8B:
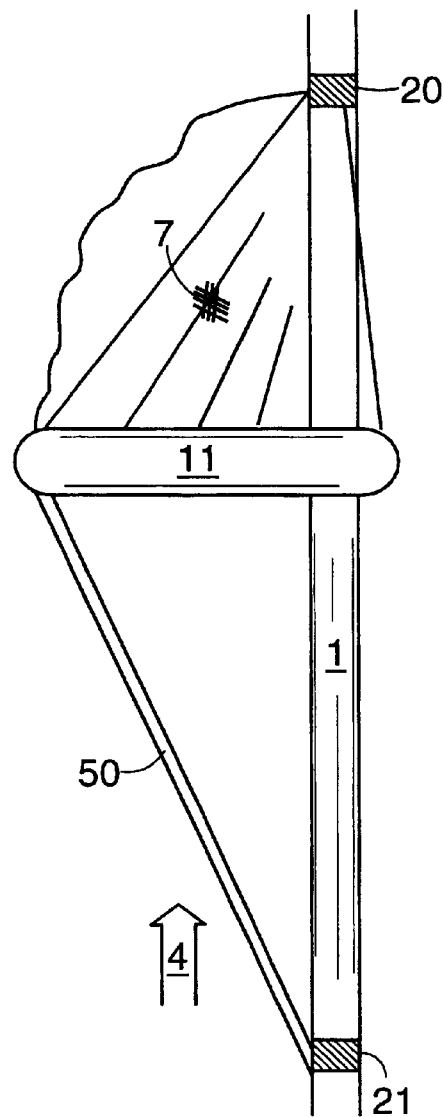
FIG. 8B is a longitudinal view of the same embodiment in the deployed condition.

FIG. 8A is a cross-sectional view of a catheter-filter set according to an embodiment of the invention, using for deployment a balloon 11 that is asymmetrically disposed with respect to the tubular member. FIG. 8B is a longitudinal view of the same embodiment in the deployed condition. FIG. 8C shows detail of the catheter-balloon interface. This embodiment increases the area available for flow through the "doughnut hole" of the balloon 11 and, like the embodiment of FIGS. 7A through 7C, avoids the need for a separate inflation tube connecting the balloon 11 with the catheter 1. In this embodiment, the catheter 1 passes through the toroidal balloon 11 at location 80 on its circumference; a seal is provided between the balloon 11 and the catheter so that the balloon can be inflated through a port as in the embodiment of FIG. 7. In the stowed position, shown in FIG. 8A, an elastic band 50 attached to the balloon 11 at a point diametrically opposite to the inflation site 80 draws the balloon 11 in the upstream direction. When and as the balloon 11 is deflated, it and filter 7 are collapsed radially against the catheter 1 bore under the force of the elastic band 50. Additional elastic bands may be optionally used on the downstream side to help gather together the filter 7 on deflation. The filter is deployed by inflation of balloon 11 through the port at location 80 as illustrated in FIG. 8B. Balloon inflation also seals the balloon 11 in a flexible manner against the wall of the vas. In the process of balloon inflation, the catheter 1 is displaced off center toward the wall of the vas so as to increase the area available for flow. All flow still passes through the filter 7.

Figure 9:
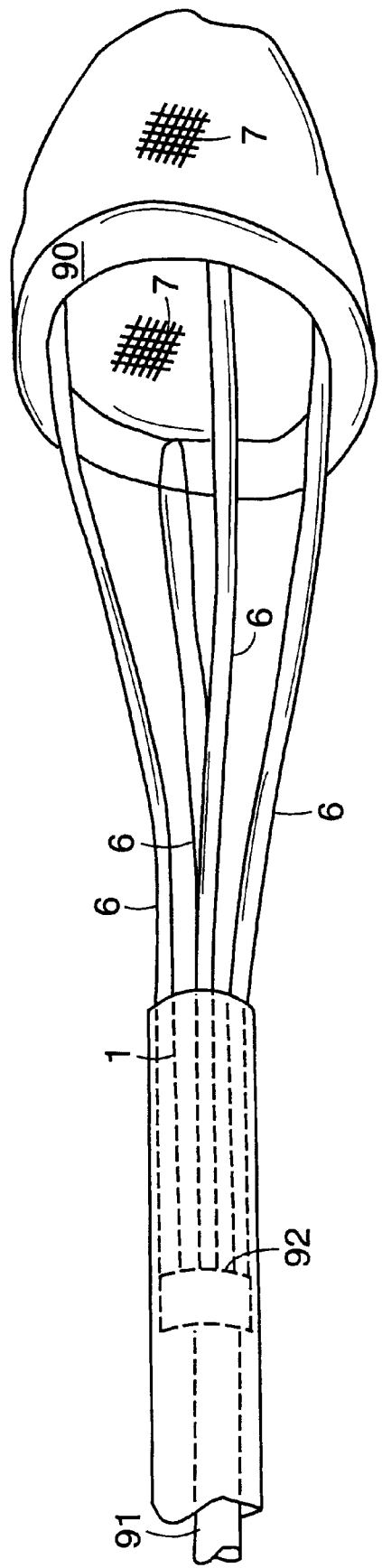
FIG. 9 is a view of a catheter-filter set according to an embodiment of the invention utilizing a retractable O-ring.

FIG. 9 is a perspective view of a catheter-filter set according to an embodiment of the invention utilizing a retractable O-ring. The downstream end of the catheter 1 is pictured at a location downstream of a suitable vas-modifying element. The filter 7 is fastened to an O-ring 90 which in turn, is coupled to a set of resilient ribs 6 (four of which are shown). When in the deployed position (shown) the ribs 6 are pushed out of the downstream end of the catheter 1. The resilience of the O-ring 90 (optionally, in combination with shape memory of the ribs 6) causes the ribs 6 to separate as the O-ring 90 deploys into its natural circular shape, producing a seal against the wall of the vas. In so doing, the O-ring 90 expands the filter 7 so that it can trap debris released from an upstream location. The filter 7 is returned to its original undeployed position by retracting the ribs 6 into the catheter 1, exerting a radially-inward force on the O-ring 90, causing it to buckle into a multi-lobed pattern with outside radial dimension much smaller than in the deployed position. The ribs 6 can be drawn into the catheter 1 by means of a stiff tether line 91 attached to the ribs 6 at their upstream end 92 within the catheter lumen. The tether line 91 must be sufficiently rigid that it can exert the force needed to deploy the filter 7 and the O-ring 90. For ease of retrieval, the filter 7 can be sheathed by a second catheter that slides on the outer bore of the catheter 1, slipping over the buckled O-ring 90 and filter 7.

Figure 10:
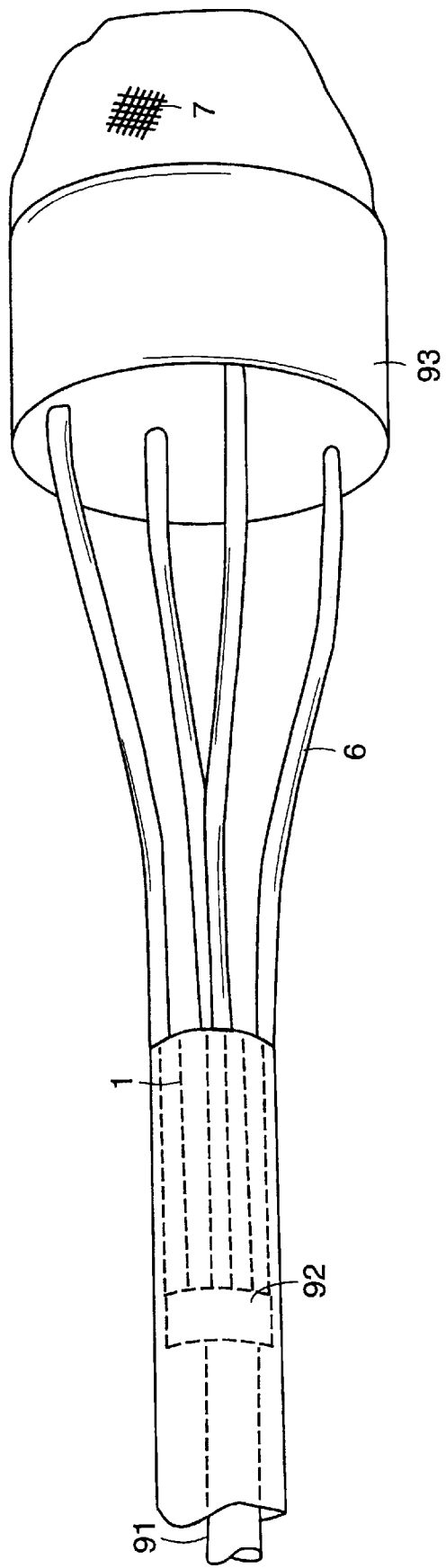
FIG. 10 is a perspective view of a catheter-filter set according to an embodiment of the invention that is similar to the embodiment of FIG. 9, but utilizing a sleeve in lieu of the O-ring.

FIG. 10 is a perspective view of a catheter-filter set according to an embodiment of the invention that is similar to the embodiment of FIG. 9, but utilizing a cylindrical sleeve 93 in lieu of the O-ring 90. An advantage of the sleeve is that the filter 7 can be entirely contained within the sleeve 93 when the ribs and filter are in the retracted position, thus eliminating the necessity for a second catheter.

Figure 11A:
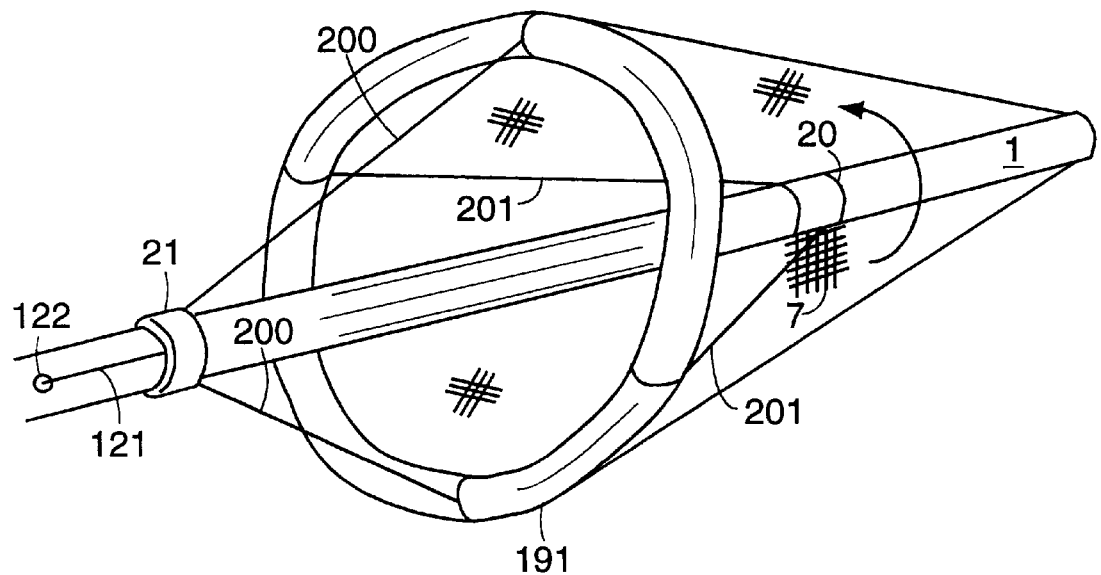
FIG. 11A is a perspective view of a catheter-filter set according to an embodiment of the invention utilizing a tethered O-ring, shown in the deployed condition.
Figure 11B:
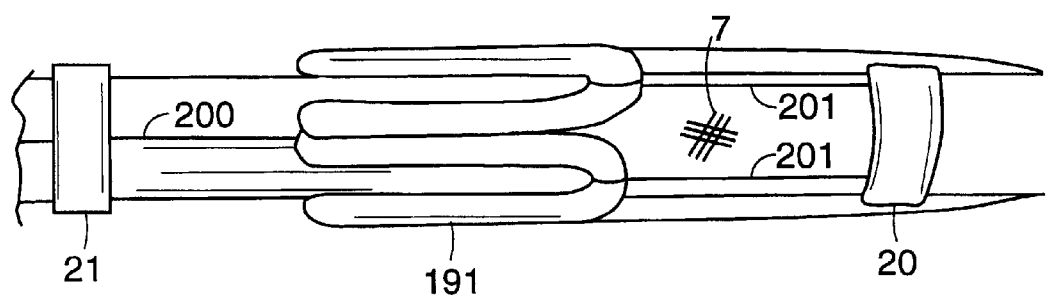
FIG. 11B is a longitudinal view of the same embodiment in the stowed condition.

FIG. 11A is a perspective view of a catheter-filter set according to an embodiment of the invention utilizing a tethered O-ring, shown in the deployed condition. FIG. 11B is a longitudinal view of the same embodiment in the stowed condition. This embodiment shows that an O-ring 191 may be employed in situations in which the filter 7 is attached upstream of the end of the catheter 1. Deployment, in this embodiment, is accomplished when the operator relaxes the force applied by the line 121 which passes through the wall of the catheter 1 at point 122. The line 121 is attached to a collar 21 that can slide freely along the bore of the catheter 1. When force is relaxed, the resilience of the O-ring 191 that exerts a tension in a plurality of tether lines 200 (two are shown) pulls the collar 21 in the downstream direction. The O-ring 191, selected to be of an outer diameter when fully extended slightly larger than the normal diameter of the vas, provides a flexible seal against the wall of the vas when the tension force in tethers 200 is reduced. A filter 7 is attached around the circumference of the O-ring 191 and is deployed when the O-ring is allowed to expand to fill the vas. The O-ring 191 is also attached to a plurality of additional tethers 201 (two are shown) that are rigidly fixed to the downstream collar 20. All tether lines 200 and 201 are inextensible and, in this embodiment, are attached at points distributed roughly equidistant around the circumference of the O-ring 191. To retract and stow the filter, the operator pulls on the line 121 and the O-ring buckles into the configuration shown in FIG. 11B due to the alternating attachments of the tether lines 200 and 201. The buckling of the O-ring 191 also helps to gather together the filter 7.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A catheter-filter set for use in a vas through which a biological fluid may flow, the vas having an interior wall, the fluid flow defining downstream and upstream directions, there being a risk of the presence of undesired particles in the fluid, the catheter-filter set comprising:
   a. a tubular member, having a lumen disposed along its length and an insertion end for insertion into the vas, the lumen defining a longitudinal axis and a radial direction perpendicular thereto;
   b. a filter, coupled to the tubular member and having a circumference, for trapping undesired particles; and
   c. a resilient member, having compliance in the radial direction, disposed circumferentially about the filter and, when deployed in the vas, forming a seal against the interior wall,
wherein the resilient member is a non-inflatable O-ring.

2. A catheter-filter set for use in a vas through which a biological fluid may flow, the vas having an interior wall, the fluid flow defining downstream and upstream directions, there being a risk of the presence of undesired particles in the fluid, the catheter-filter set comprising:
   a. a tubular member, having a lumen disposed along its length and an insertion end for insertion into the vas, the lumen defining a longitudinal axis and a radial direction perpendicular thereto;
   b. a filter, coupled to the tubular member and having a circumference, for trapping undesired particles; and
   c. a resilient member, having compliance in the radial direction, disposed circumferentially about the filter and, when deployed in the vas, forming a seal against the interior wall,
wherein the resilient member is a non-inflatable sleeve.

3. A catheter-filter set for use in a vas through which a biological fluid may flow, the vas having an interior wall, the fluid flow defining downstream and upstream directions, there being a risk of the presence of undesired particles in the fluid, the catheter-filter set comprising:
   a. a tubular member, having a lumen disposed along its length and an insertion end for insertion into the vas, the lumen defining a longitudinal axis and a radial direction perpendicular thereto;
   b. a filter, coupled to the tubular member and having a circumference, for trapping undesired particles;
   c. a balloon having an interior for receiving an inflation fluid and a shape so that when the balloon is inflated there is provided a passageway permitting fluid flow through the filter; and d. an elastic member coupled to the balloon and the tubular member for causing the balloon to be radially confined when not deployed.

4. A catheter-filter set for use in a vas through which a biological fluid may flow, the vas having an interior wall, the fluid flow defining downstream and upstream directions, there being a risk of the presence of undesired particles in the fluid, the catheter-filter set comprising:

a. a tubular member, having a lumen disposed along its length and an insertion end for insertion into the vas, the lumen defining a longitudinal axis and a radial direction perpendicular thereto;

b. a filter, coupled to the tubular member and having a circumference, for trapping undesired particles;

c. a toroidal-shaped balloon having an interior for receiving an inflation fluid, the interior having a cross-section, so that when the balloon is inflated there is provided a passageway permitting fluid flow through the filter, and wherein the balloon has anisotropic elasticity so that during inflation its interior cross-section expands relatively less than its radial extent.

5. A catheter-filter set for use in a vas through which a biological fluid may flow, the vas having an interior wall, the fluid flow defining downstream and upstream directions, there being a risk of the presence of undesired particles in the fluid, the catheter-filter set comprising:

a. a tubular member, having a first lumen disposed along its length, an insertion end for insertion into and a retraction end for retraction out of the vas, the lumen defining a longitudinal axis and a radial direction perpendicular thereto;

b. a filter, coupled to the tubular member proximal to the insertion end, wherein the filter has a stowed position wherein the filter is radially confined so that the catheter-filter set may be inserted into and removed from the vas, and a deployed position, wherein the filter is radially expanded; and c. a non-inflatable actuator, coupled to the filter, for causing the filter to move from the stowed position to the deployed position;

wherein, absent operation of the actuator, the filter is biased to be in the stowed position.

6. A catheter-filter set according to claim 5, further comprising:

d. a vas conditions-modifying element, associated with the tubular member and located upstream from the filter.

7. A catheter-filter set according to claim 5 wherein element (d) is an angioplasty balloon.

8. A catheter-filter set according to claim 5, wherein the tubular member has a second lumen, the second lumen having an inlet upstream from the vas conditions-modifying element and an outlet downstream from the filter, permitting unimpeded, downstream fluid flow to bypass the filter.

9. A catheter-filter set according to claim 8, wherein the second lumen has a diameter of from approximately 1 mm to approximately 2 mm.

10. A catheter-filter set according to claim 5, further comprising:

d. a plurality of resilient ribs, each rib having a first end coupled to the tubular member, each rib also coupled to the filter, the ribs having a stowed condition in which they are parallel to the longitudinal axis and having a deployed condition in which at least a portion of each rib is disposed radially outward from the tubular member.

11. A catheter-filter set according to claim 10, wherein the filter, in the deployed position, has a maximum radial extent and each rib, in the deployed condition, radially extends a distance less than the maximum radial extent of the filter.

12. A catheter-filter set according to claim 10, wherein each rib has a second end slidably mounted on the tubular member and coupled to the actuator.

13. A catheter-filter set according to claim 12, wherein each rib is coupled to a collar slidably mounted on the tubular member.

14. A catheter-filter set according to claim 10, further comprising:

e. a vas conditions-modifying element, associated with the tubular member and located upstream from the filter.

15. A catheter-filter set according to claim 14 wherein element (e) is an angioplasty balloon.

16. A catheter-filter set according to claim 14, wherein the tubular member has a second lumen, the second lumen having an inlet upstream from the vas conditions-modifying element and an outlet downstream from the filter, permitting unimpeded, downstream fluid flow to bypass the filter.

17. A catheter-filter set according to claim 16, wherein the second lumen has a diameter of from approximately 1 mm to approximately 2 mm.

18. A catheter-filter set according to claim 5, further comprising:

d. a resilient member, having compliance in the radial direction, disposed circumferentially about the filter and, when deployed in the vas, forming a seal against the interior wall.

19. A catheter-filter set according to claim 18, further comprising:

e. a plurality of resilient ribs, each rib having a first end coupled to the tubular member, each rib also coupled to the filter, the ribs having a stowed condition in which they are parallel to the longitudinal axis and having a deployed condition in which at least a portion of each rib is disposed radially outward from the tubular member.

20. A catheter-filter set according to claim 19, wherein the filter, in the deployed position, has a maximum radial extent and each rib, in the deployed condition, radially extends a distance less than the maximum radial extent of the filter.

21. A catheter-filter set according to claim 19, wherein each rib has a second end slidably mounted on the tubular member and coupled to the actuator.

22. A catheter-filter set according to claim 21, wherein each rib is coupled to a collar slidably mounted on the tubular member.

23. A catheter-filter set according to claim 19, further comprising:

f. a vas conditions-modifying element, associated with the tubular member and located upstream from the filter.

24. A catheter-filter set according to claim 23 wherein element (f) is an angioplasty balloon.

25. A catheter-filter set according to claim 19, wherein the tubular member has a second lumen, the second lumen having an inlet upstream from the vas conditions-modifying element and an outlet downstream from the filter, permitting unimpeded, downstream fluid flow to bypass the filter.

26. A catheter-filter set according to claim 25, wherein the second lumen has a diameter of from approximately 1 mm to approximately 2 mm.

27. A catheter-filter set according to claim 18, wherein the resilient member is an O-ring.

28. A catheter-filter set according to claim 18, wherein the resilient member is a sleeve.

29. A catheter-filter set according to claim 18, wherein the resilient member is a resilient balloon having an interior for receiving an inflation fluid and a shape so that when the resilient balloon is inflated there is provided a passageway permitting fluid flow through the filter.

30. A catheter-filter set according to claim 29, wherein the resilient balloon is toroidal and its interior has a cross-section.

31. A catheter-filter set according to claim 30, wherein the resilient balloon has anisotropic elasticity so that during inflation its interior cross-section expands relatively less than its radial extent.

* * * * *